United States Patent
Yin et al.

(10) Patent No.: US 6,709,271 B2
(45) Date of Patent: Mar. 23, 2004

(54) LOW SHRINKAGE DENTAL COMPOSITE

(75) Inventors: Rui Yin, Buffalo Grove, IL (US);
Byoung In Suh, Oak Brook, IL (US);
Louis Sharp, Libertyville, IL (US);
Amer Tiba, Schaumburg, IL (US)

(73) Assignee: Bisco, Inc., Schaumburgh, IL (US)

( * ) Notice: Subject to any disclaimer, the term of this patent is extended or adjusted under 35 U.S.C. 154(b) by 94 days.

(21) Appl. No.: 09/989,601

(22) Filed: Nov. 20, 2001

(65) Prior Publication Data

US 2003/0175660 A1 Sep. 18, 2003

(51) Int. Cl.$^7$ ................................................. A61C 5/00
(52) U.S. Cl. ..................................... 433/228.1; 523/116
(58) Field of Search ............................ 433/228.1, 226, 433/222.1; 523/116, 115, 118

(56) References Cited

U.S. PATENT DOCUMENTS

| | | | |
|---|---|---|---|
| 4,437,836 A | 3/1984 | Schmitz-Josten et al. | 433/199 |
| 4,439,380 A | 3/1984 | Michl et al. | 264/16 |
| 4,816,495 A | 3/1989 | Blackwell et al. | 522/14 |
| 6,306,927 B1 | 10/2001 | Blackwell et al. | 523/116 |
| 6,313,192 B1 * | 11/2001 | Anstice et al. | 523/116 |
| 6,417,246 B1 * | 7/2002 | Jia et al. | 523/113 |

FOREIGN PATENT DOCUMENTS

| | | |
|---|---|---|
| EP | 0 345 581 A2 | 5/1989 |
| EP | 0 530 926 A1 | 9/1992 |
| EP | 0732 099 A2 | 3/1996 |
| WO | WO 01/30304 A1 | 5/2001 |

OTHER PUBLICATIONS

Bausch et al., "Clinical significance of polymerization shrinkage of composite resins", J.Prosth.Dent 48(0): 59–67 (Jul. 1982).
"Clinical status of ten dentin adhesive systems" Journal of Dental Research, vol. 73, 1690–1702.
Davidson et al., "The Competition between the Composite–Dentin Bond Strength and the Polymerization Contraction Stress", J.Dent.Res. 63(12): 1396–1399 (Dec. 1984).
Davidson et al., "Relaxation of Polymerization Stresses by Flow in Dental Composites", J.Dent.Res. 63(2): 146–148 (Feb. 1984).
Davidson, "Resisting the curing contraction with adhesive composites", J.Prosth.Dent. 55(1): 446–447 (Apr. 1986).
Feilzer et al., "Setting Stress in Composite Resins in Relation to Configuration of the Restoration", J.Dent.Res. 66(11): 1636–1639 (Nov. 1987).
Kemp–Scholte et al., "Complete Marginal Seal of Class V Resin Composite Restorations Effected by Increased Flexibility", J.Dent.Res. 69(6): 1240–1243 (Jun. 1990).
Kemp–Scholte et al., "Marginal Sealing of Curing Contraction Gaps in Class V Composite Resin Restorations", J.Dent.Res. 67(5): 841–845 (May 1988).
International Search Report dated Jul. 25, 2002.

\* cited by examiner

Primary Examiner—Kevin Shaver
Assistant Examiner—Melba Bumgarner
(74) Attorney, Agent, or Firm—Howrey Simon Arnold & White LLP

(57) ABSTRACT

Dental composite compositions, restorative compositions, and methods for their use are provided. The compositions can contain (a) from about 1 to about 35 weight percent of a monomer portion containing at least one monomer having a functional group capable of undergoing polymerization; (b) from about 75 to about 95 weight percent of a filler portion, the filler portion containing at least a spherical filler portion having at least one spherical filler particle component; and (c) from about 0.01 to about 10 weight percent of a polymerization catalyst portion containing at least one catalyst capable of assisting in the polymerization of the functional group of the monomer portion and hardening of the composite after application of the composite to a tooth surface or other dental surface. The spherical filler portion is present in an amount sufficient to reduce shrinkage of the composite after polymerization to about 1.8 percent or less. Compositions according to the invention are useful in Class I, II, IV, V, Core build-ups, and other types of dental restorations where maximum strength and polishability are desired. Methods for using such compositions in such restorative procedures are also provided.

35 Claims, No Drawings

LOW SHRINKAGE DENTAL COMPOSITE

FIELD OF THE INVENTION

The present invention relates generally to dental compositions and methods, and more particularly to dental restorative compositions and restorative methods using such compositions.

BACKGROUND OF THE INVENTION

Moden dental restorative procedures have recently gravitated toward the use of polymerizable resin compositions in place of metal amalgams and other traditional dental fillers. For example, in filling cavities or other defects in the tooth's surface, many dental professionals now use polymerizable resin compositions containing inorganic glass fillers to impart desired compressive strength in place of metal amalgams. Such filled polymerizable materials are easy to apply, can be colored and shaped to correspond to the original tooth surface, and often exhibit chemical adhesion to the tooth surface when polymerized as opposed to the metallic appearance and mechanical adhesion of metal amalgams.

Although filled polymerizable composite resin compositions are in widespread use, certain problems are recognized to exist due to the nature of the compositions. For example, because such composites typically depend on polymerization reactions to effect hardening of the resin in place on the tooth surface, they exert stresses on the adjacent tooth structure due to shrinkage which occurs during polymerization as the monomers move from their free liquid state into their more dense, cross-linked polymerized state. Such shrinkage and resultant stresses are often considerable, particularly in a so-called "Class V" type restoration, wherein the restoration is being effected at the dentin-enamel junction at the cervical region of the tooth, and also in so-called "Class I" restorations such as deep cavities involving restorations contacting opposing walls of the tooth. See e.g., Feilzer et al., "Setting Stress in Composite Resins in Relation to Configuration of the Restoration", J.Dent.Res. 66(11): 1636–1639 (November, 1987) and Davidson et al. "The Competition between the Composite-Dentin Bond Strength and the Polymerization Contraction Stress, J.Dent.Res. 63(12): 13961399 (December 1984), the disclosures of which are hereby incorporated by reference. Such shrinkage and related stresses have been reported as causing separation of the restoration from at least the dentin surface of the tooth, leading to the creation of marginal gaps at the interface between the restorative and the adjacent tooth surface and causing microleakage. Id. See also, Bausch et al., "Clinical significance of polymerization shrinkage of composite resins", J.Pros. Dent. 480): 59–67 (July, 1982), the disclosure of which is hereby incorporated by reference. Current commercial universal hybrid composites shrink from 2.2 to about 3.5% by volume fraction.

In response to these problems, much effort has focused on creation of compositions and methods to reduce or eliminate shrinkage-related stresses and marginal gaps in dental restorations. Reported approaches have included reliance on the "flow" of the composite during chemical self-curing, which proceeds slowly, (See, Davidson et al., "The Relaxation of Polymerization Stresses by Flow in Dental Composites", J.Dent.Res. 63(2): 146–148 (February, 1984)) or by incremental insertion of the composite in the restorative site (See Davidson, "Resisting the Curing Contraction with Adhesive Composites", J.Prosth.Dent. 55(1): 446–447 (April 1986.) The first "flow" study did not, however, investigate composite-dentin bonding and whether "flow" would obviate gap creation. Flow dissipation of shrinkage is also believed to be limited to self-cure chemical polymerization, which occurs over a period of at least several minutes, as opposed to light or heat induced polymerization, which is often completed in a matter of 12 minutes or less.

Others have proposed multi-step application procedures using low viscosity, unfilled resins to seal the marginal gaps directly after initial curing of the composite, (See, Kemp-Scholte et al., "Marginal Sealing of Curing Contraction Gaps in Class V Composite Resin Restorations", J.Dent.Res. 67(5): 841–845 (May, 1988)), or use of so-called "flexible" intermediate layers of unfilled resins or light-cured glass ionomer layers applied as a thin liner layer between the tooth surface and the composite. See, Kemp-Scholte et al., "Complete Marginal Seal of Class V Resin Composite Restorations Effected by Increased Flexibility", J.Dent.Res. 69(6); 1240–1243 (June 1990). The later study reported that certain stress release liners, the traditional glass ionomers (Ioline), actually cracked and exhibited cohesive failures. Certain unfilled resins are also known to exhibit significant shrinkage and, generally become brittle upon curing. These multi-step, multi-material approaches also introduce complexity into the dental restoration process in terms of number of steps, materials, and increase the time spent and cost incurred by the dental professional and patient in the treatment process. In addition to exhibiting good adhesion and bonding, composites and other polymerizable dental restorative material must also withstand the compressive, tensile and other forces experienced by the tooth surface in the mouth. For example, considerable compressive forces are generated by contact from other teeth during chewing and other mouth movements. The restorative may also experience tensile and abrasive forces in the mouth depending on its location on or within the tooth's surfaces. In, for example, Class V restorations, shear forces are also experienced in the restoration during mastication. Such shear forces must also be absorbed and/or dissipated or the restoration may fail. See "Clinical Status of Praesens of Dentine Adhesives" pp. 113–115, the disclosure of which is hereby incorporated by reference.

There exists, therefore, a need in the art for dental composite compositions and other restorative, compositions, which reduce the volumetric shrinkage and contraction stress upon polymerization of the dental composites. In addition these dental composite compositions must exhibit good bond strength, good tensile and compressive strengths, and be easy to apply and use in dental restorative procedures.

SUMMARY OF THE INVENTION

It is an object of the present invention to provide dental composite compositions and restorative compositions with a high filler content to reduce the polymerization shrinkage and the risk of microleakage and which still exhibit easy handling, good bonding to tooth, dentin and enamel, and which also possess good tensile and compressive strengths.

It is an object of the present invention to include a filler portion comprising one or more suitable spherical filler materials, such as barium or other glasses, in amounts which total from about 20 to about 40.0 weight percent of the dental composite compositions and restorative compositions to improve handling properties and increase filler loading.

It is an additional object of the present invention to include a polyurethane dimethacrylate oligomer with a soft segment and that has a relatively high average molecular weight (number average) from at least about 1500 or higher in dental composite compositions and restorative compositions to reduce the polymerization shrinkage and lower the contraction stress.

It is also an object of the present invention to include a multifunctional monomer portion from about 1 to about 35 weight percent, and a monofunctional monomer portion comprising one or more suitable comonomers in weight amounts which total about 1 to about 10 weight percent of the composition to control the resin viscosity and the cross-linking density of the cured polymer. Preferably the monomers are capable of undergoing polymerization reactions with the oligomer portion.

It is also an object of the present invention to include suitable polymerization catalyst systems or compositions, such as chemical self-cure initiators, light-activated initiators and/or heat-activated polymerization initiators in the dental composite compositions and restorative compositions.

It is an important aspect of the present invention wherein compositions of the present invention are used as composite restorative materials. In addition, dental restorative methods are contemplated wherein compositions of the present invention are applied as liners in restoration sites and accept conventional composite restorative compositions.

DETAILED DESCRIPTION OF THE INVENTION

The compositions of the present invention and methods for their use have particular application in the field or restorative dentistry. Preferred compositions according to the present invention comprise a spherical filler portion, a multifunctional and/or monofunctional comonomer portion, and a polymerization catalyst portion comprising a polymerization compound or system. Optionally, the compositions may also include a unique polyurethane dimethacrylate ester (PUDMA) oligomer portion, antimicrobial agents, opaquifiers, fluoride-release agents, colorants and other components, which impart desirable properties to the composition. Such additional agents may be incorporated into one or more of the monomer, comonomer or filler portions of the compositions, or may be added in small amounts to the composition during formulation.

The unique polyurethane dimethacrylate ester (PUDMA) oligomer, which is used in the composition and methods of the present invention, is a polyurethane oligomeric resin with dimethacrylate and which incorporates phenyl groups as a hard segment and ethylene glycol or polymethylene as a soft segment. The PUDMA oligomer of the present invention may be manufactured in the laboratory by well-known methods or may be purchased from commercial sources such as Methacrylate Ester IRR456) from UCB Chemicals Corporation, Drogenbos, Belgium. Such commercial monomers are available in average molecular weights (number average) of from about 1500 to about 5000. Those of ordinary skill in the art will recognize that higher molecular weight oligomers of about 1500 or higher may require dissolution in a suitable diluent monomer before formulation in composition according to the present invention. At present, oligomers having an average molecular weight of less than 10,000 and greater than 1000, i.e. from about 1000 to about 2000 are more preferred in the present invention for reasons such as ease of formulation. PUDMA having an average molecular weight of about 1500 is presently a preferred oligomer. Presently preferred amounts of oligomer in compositions of the present invention are from about 1 to about 15 weight percent of the total composition. Presently more preferred amounts are in the range of about 7 to about 12 weight percent of the composition.

Preferred fillers according to the present invention include one or more well-known spherical particles. For example, spherical particles are silanated oxides of aluminum, zirconium and silicon, silicate glasses, and barium or strontium glasses. The use of spherical particles in the compositions of the present invention is presently preferred to control and improve handling characteristics, such as bulk and consistency, and improve the filler packing for better restoration placement in cavity preparations by minimizing the flow and/or slump of the composition. The low surface area (1.5 $m^2$/g) of the spherical particles in contrast with similar sized (1.0±0.5 $\mu$m) glass fillers (10 $m^2$/g) also requires less resin to obtain a complete wetting, so that a relatively high filler loading can be achieved. In addition, spherical particles generally have lower impurity levels, less than 0.2%, and a refractive index that is lower than the resin. In most composites, fillers have a higher refractive index than the resin. Presently preferred spherical particles include TC3 from Suzuki Oil & Fat Corporation, Hyogo, Japan, one of only a few companies that make a small spherical filler.

It is presently contemplated that such spherical fillers be present in amount sufficient to reduce the amount of volumetric shrinkage of the composite to less than 2% after polymerization. At present, spherical fillers in the amounts of from about 20 to about 40 weight percent of the composite are preferred, with a range of from about 20 to about 30 weight percent being more preferred. However, depending on the nature and amounts of other fillers present in the composite, the amount of spherical filler may be present in greater or smaller amounts. For example, it is contemplated that a very small size spherical filler might be used to replace all or almost all of the sub-micron filler component identified below. A relatively larger spherical particle might be used to replace part of the conventional filler identified below. The foregoing indicates that spherical filler might be present in amounts of from about 5 to about 75 weight percent in such composites with such other fillers.

In addition to the use of spherical particles, the use of other, sub-micron size fillers in the compositions of the present invention optionally may be used in ranges of from about 5 to about 50 weight percent, and more preferably from about 15 to about 40 weight percent of the composite. For example, sub-micron size fillers are also silanated oxides of aluminum, zirconium and silicon, silicate glasses, and barium or strontium glasses. The use of other, sub-micron size fillers is presently preferred to minimize surface wear and "plucking" of filler components from the restorative surface, as well as imparting a surface which may be easily polished by the dental professional. Preferred contemplated filler particles have an average size of about 0.020 to 0.080 microns. Presently more preferred fillers have an average particle size of about 0.04 to about 0.08 microns Conventional fillers may also be used in combination with the spherical fillers and/or sub-micron fillers. For example, SR Glass RGW EG 2993 may be used in combination with either or both other types of fillers. Such conventional fillers are well-known in the art, and may be present in amount of from about 5 to about 75% of the composite, it being understood that its amount being dependent in part on the amount of spherical filler present in the composite One or more of the aforementioned fillers comprising the filler portion may also include caries inhibiting agents such as slow releasing fluoride agents to help inhibit caries from forming in the adjacent tooth structure. For example, glass ionomer IX 1944 from Ferro Corporation, Cleveland, Ohio, which contains a slow release fluoride agent, is expected to have utility in the present invention.

The filler or fillers are present at about 75 to about 95 weight percent of the contemplated compositions of the present invention, and are more preferably present at about 80 to about 92 or from about 84 to about 92 weight percent of the composition. The amount of the filler component is adjusted in view of the other components of the composition and in view of the intended use of the composition, it being well known in the art that higher filler amounts generally impart higher compressive strengths to a composition, but also tend to increase viscosity and decrease flowablity of the composition. Presently preferred fillers include silica particles from Suzuki Oil & Fat Corporation, Hyogo, Japan; silanated submicron glasses such as OX-50 or Aerosil R972 from DeGussa, Richfield Park, N.J.; and porcelain ground strontium glass such as EG2933 RWG from Ferro Electronic Glass, Cleveland, Ohio. Optionally, the filler portion is formulated to include appropriate coloring agents in varying amounts to provide the dental professional with a range of colors in the composition, which may be selected for compatibility with the shade of the patient's tooth undergoing restoration. Such coloring or tint agents are well known in the art, and may be included in small amount of about 1 weight percent or less of the total composition. Such fillers can also be selected to be radio opaque. For example, appropriate amounts of radio opaque barium, strontium or zirconium glass may be used as all or part of the filler portion, which can assist the dental professional in his or her post-treatment examination of the patient.

Preferred fillers according this invention may also include one or more glass fibers. For example, glass fibers, silanated oxide of aluminum, silicon and titanium may be employed. The use of glass fiber in the composition of present invention is presently preferred to increase filler packing and improve filler self-orientation for high filler loading. The low surface area (0.4 m$^2$/g) of glass fiber with diameter (2–3 $\mu$m) and length (20 $\mu$m) requires less resin to obtain complete wetting, so that a relatively high filler loading can be achieved. Presently preferred glass fibers include Fiberfrax milled from Unifrax Corporation, Niagara Fall, N.Y. Presently preferred composites according to the invention include filler portions comprising the following amounts of glass fibers with spherical fillers and submicron filler components, it being understood that other fillers and fibers could be substituted depending on the nature of the desired composite:

|  | Fibertrax | TC3 | OX-50 |
| --- | --- | --- | --- |
| Preferred range 1 | 20–80 wt % | 5–80 wt % | 0–40 wt % |
| Preferred range 2 | 30–50 wt % | 20–40 wt % | 10–25 wt % |
| Preferred range 3 | 40–45 wt % | 30–38 wt % | 15–20 wt % |

In general, a highly loaded composite looks very dry and is very hard to handle. Preferred compositions of the present invention also include suitable monomer(s) containing one or more functional groups capable of polymerization reaction with one or more of the monomers in the monomer portion of the composition, and more preferably capable of polymerizing with the PUDMA oligomer. For example, a monofunctional may be used to act as a diluent to control or reduce the viscosity of the resin as well as to provide fewer polymerization sites, both of which assist in formulating the composition. The addition of a viscosity controlling monofunctional monomer makes the composition and composites of the present invention as easy to work with as normal hybrid composites. Alternatively and/or additionally, a multifunctional comonomer may be used as a diluent as well as to build up a better cross-linking structure in the polymer matrix. This structure plays a very important role in the mechanical properties of the dental materials. It is presently preferred that the multifunctional comonomer(s) be selected such that they contain two or more functional groups which are capable of undergoing polymerization reactions with the other monomer(s) and oligomer present in the composite to help impart good flexure and tensile strength to the composition as well a relatively high degree of cross-linking throughout the composition. Such monofunctional and multifunctional diluent comonomer(s) are preferably present in amount of from about 1 to about 10 weight percent of the composition, and more preferably less than about 5 percent. The amount of the monomer or comonomer portion in the overall composition is dependent in part on the amount of filler and oligomer in the composition and in part on the desired viscosity and flow characteristics of the composition, it being presently preferred that such amounts be in the range of from about 1 to about 35 weight percent of the composite, preferably from about 1 to about 20 weight percent, and more preferably from about 8 to about 15 weight percent Suitable monofunctional and multifunctional monomers may include well-known mono-, di-, tri-, and tetraacrylate and methacrylates such as 2,2-bis [4-(3-methacryloxy-2-hydroxypropoxy)phenyl]-propane (BIS-GMA), Bisphenol A dimethacrylate (Bis A Dima), ethoxylated Bis "A" Dima (Dima), neopentylglycol dimethacrylate, decanediol-1,10-dimethacrylate, dodecanediol-1,12-dimethacrylate, 1,4-butanediol dimethacrylate, ethyleneglycol dimethacrylate, diethyleneglycol dimethacrylate, triethylene glycol dimethacrylate (TEGDMA), tetraethyleneglycol dimethacrylate), polyethyleneglycol dimethacrylate, propyleneglycol dimethacrylate, dipropyleneglycol dimethacrylate, tripropyleneglycol dimethacrylate, tetrapropyleneglycol dimethacrylate, polypropyleneglycol dimethacrylate, hexamethyleneglycol dimethacrylate 2,2-bis(4-methacryloxyphenyl)propane, 2,2-bis(4-methacryloxyethoxyphenyl)propane, 1,2-bis(3-methacryloxy-2-hydroxypropoxy)ethane, CPDM-the reaction product of cyclopentane tetracarboxylic acid dianhydride and 2 moles of hydroxyethyl methacrylate (HEMA), tetrahydrofurfuryl cyclohexene dimethacrylate (TCDM)-the reaction product of Epiclon B-4400 (Dainippon Inc. and Chemicals Inc., Ft. Lee, N.J.) with 2 moles of HEMA, hexa-functional methacrylate ester, 2,2-bis(4-methacryloxyphenyl)-propane, 2-hydroxy-1,3-dimethacryloxypropane, di-2 methacryloxyethyl-2,2,4-trimethylhexamethylene dicarbamate (UDMA), di-2 methacryloxyethylisophorone dicarbamate, tetrahudrofufryl methacrylate (THFMA) and di-2-methacryloxyethyl-2,4- or 2,6-tolylene dicarbamate. Of the above monomers, the use of ethoxylated Bis A Dima and/or THFMA are presently preferred.

Presently preferred comonomer portions include the admixture of two or more of such monomers. For example, Ethoxylated Bisphenol A Dimethacrylate and Hexa-function methacrylate ester in a ratio of from about 1:1 to about 4:1 have been found to have utility in the present invention.

Optionally, one or more of the monomer compounds may include a caries inhibiting agent that helps to prevent or inhibit caries formation in the adjacent tooth structure. For example, the fluoride release monomer disclosed in U.S. Pat. No. 5,037,638, whose disclosure is incorporated by reference, may have utility in the present invention as part of the monomer portion of the composition.

A polymerization catalyst compound, composition or system is also included in the preferred compositions of the present invention. Such polymerization compounds, compositions or systems are well known in the art. They generally fall within one of three categories: (1) self-curing chemical systems that initiate polymerization upon admixing two or more compounds; (2) light-initiated polymerization systems; and (3) heat-initiated polymerization systems. A polymerization system employing two or more initiators, i.e. light/self cure or light/heat initiated systems is also contemplated to give the dental professional additional flexibility in the restorative procedures.

Exemplary self-curing systems include traditional free radical polymerization initiators normally used with polymerizable ethylenically unsaturated materials and resins. For example, organic peroxide initiators and amine accelerations such as those disclosed in U.S. Pat. No. 4,816,495, whose disclosure is hereby incorporated by reference, may be used, and, as taught therein, packaged separately from the polymerizable monomer components of the system and admixed with the monomers shortly before application to the tooth or dental appliance.

A light or photo-curing or photosensitive polymerization initiation and curing system is also included in a contemplated light-curable composition of the present invention. A contemplated photo-curing system is activated to harden and cure the composition by irradiation with visible or UV light. For example, visible light of a wavelength of about 400 to about 500 nm initiates rapid and efficient curing.

A light or photo-curing or photosensitive polymerization initiation and curing system according to preferred embodiments of the present invention include alpha-diketone light-sensitive initiator compounds such as benzophenone or a derivative, or an 1,2-diketone such as benzil or camphorquinone (CQ) and CQ derivatives and certain tertiary aromatic amine polymerization accelerator compounds. Preferably, photo-initiator systems according to the invention are sensitive to visible light and possibly into a range of other wavelength light that is not harmful to a patient undergoing a dental procedure. Some compounds that may be suitable ultraviolet light-sensitive initiators are 1,2-diketones, benzophenones, substituted benzophenones, benzoin methyl ether, isopropoxybenzoin, benzoin phenyl ether, and benzoin isobutyl ether. Camphorquinone or a CQ derivative is presently preferred.

Presently preferred CQ or CQ derivatives may be added to the composition of the present invention in concentrations that range from about 0.01 wt. % to about 5 wt. %, more preferably from about 0.01 wt. % to about 2 wt. %, and presently most preferably from about 0.01 wt. % to about 1.0 wt. % of the total composition.

As mentioned above a tertiary amine reductant or its salt is also included. Exemplary tertiary amines include tributylamine, tripropylamine, N-alkyldialkanol amines such as N-methyldiethanolamine, N-propyldiethanolamine, N-ethyldiisopropanolamine and trialkylanol amines such as triethanolamine and triisopropanolamine. Further useful tertiary amines are specifically disclosed in U.S. Pat. Nos. 4,439,380 and 4,437,836 and 4,816,495. Ethyl-4-dimethylamino benzoate (EDMAB) is a presently preferred tertiary amine reductant.

Presently preferred concentrations of tertiary aromatic amine compounds of the present invention of the formula identified above are from about 0.01 wt. % to about 10 wt. %, more preferably from about 0.05 wt. % to about 5 wt. % and presently most preferably from about 0.1 wt. % to about 2 wt. % of the total composition. The amount of each component of the photo-initiator system depends in part on the amount of monomer present in the solution whose polymerization is to be catalyzed. Particularly preferred photo-initiator systems include CQ and ethyl 4-dimethylaminobenzoate (EDMAB). Other preferred photoinitiators include Darocur 4265 (Ciba-Geigy) and Lucirin TPO (BASF.). In usual practice, both components of the photo-curing system constitute less than about two percent of the weight of the dental compositions of the present invention, and more preferably less than about 1 weight percent.

The photo-curing system is present in an amount sufficient to cure the composite to a desired strength within about two minutes upon irradiation with light as above. More preferably, the cure time is less than about one minute, and most preferably about 20 to about 30 seconds.

Heat-initiated polymerization systems are also contemplated in the compositions of the present invention. Preferred heat initiators will initiate curing at around 60 to 150 degrees Centigrade, and more preferably about 100 to 130 degrees Centigrade. Such systems include benzoyl peroxide, t-butyl peroxybenzoate, 1,1-di(tert-butyl)peroxide and other well-known catalysts capable of initiating polymerization of ethylenically unsaturated groups or resins.

Still further ingredients such as pigments, tints, stabilizers, surfactants, fluoride release agents and thickening agents may be added to the composition to enhance its stability, color and beneficial properties. For example, well-known UV absorbers such as Uvinul 3000 available from BASF Corp. can be present at less than about 0.5 weight percent, and polymerization inhibitors such as hydroquinone monomethyl ether (MEHQ) or 2,6-di-tert-butyl-4-methylphenol (BHT) that can be present at less than 0.1 weight percent, and more usually at less than 0.01 weight percent in the composition. Uvinul-3000 is preferred as the light stabilizer and MEHQ is preferred as the polymerization inhibitor.

As indicated above, it is also contemplated that the polymerization initiator system of the present invention may include two or more initiators in the composition. For example, a combination of a light cure initiator system utilizing CQ alone or in combination with a tertiary amine reductant along with, a heat curing agent such as t-butyl peroxybenzoate is expected to have utility in the present invention. Such multi-initiator systems may have utility in that they may include both a rapid cure initiator (light or heat cure) to impart significant polymerization in the dental office or dental laboratory. For example, a light cure system in combination with a longer time self-cure initiator, which continues to cause further polymerization after the patient leaves the office and further secures the restorative to the tooth structure, is also contemplated.

Such dual cure light/heat systems, as well as their respective single initiator systems, are also desirable in that they may be formulated and packaged in one container or syringe, thereby avoiding the need for mixing by the dental professional before application. For example, as set out in the following examples, such one-component systems exhibit good shelf life of more than a year when stored away from light at room temperature. If self-curing compositions are desired, the self-curing initiator may be packaged in one of two containers separately from the polymerizable components of the composition, with the contents of both containers being admixed shortly before use in the dental office.

Preferred methods of use of the aforementioned compositions include their use as composite in classic dental restorative procedures such as Class V restorations. Such methods include the usual cleaning and preparation of the tooth surface, followed optionally and preferably by application of a dental adhesive composition, followed by application and curing of the dental compositions indicated above. For example, prepared restorative sites may be pre-treated with dental bonding adhesive systems such as "One Step" or "ALL BOND 2" from Bisco, Inc., Itasca, Ill. according to the manufacturer's instructions. Compositions according to the present invention are then applied to the tooth, preferably by syringe in incremental layers of about 0.5 to about 2 mm and cured for about 20–40 seconds (depending on the shade of the composition, darker having higher application times), followed by additional layers and curing until the cavity is completely filled to the cavosurface margin. Any excess V material is removed immediately from the surface and the restoration is finished and polished by conventional techniques such as diamonds, discs and polishing pastes. Such finishing also removes any oxygen-inhibited uncured or partially cured layer on the surface of the restoration, which if left in place, might cause staining, of the surface over time.

It will also be appreciated by those skilled in the art that the dental compositions and the methods of the present invention have significant utility in other restorative applications.

For example, compositions of the invention may also be used as liners in Class I, II or III restorations. In Class I and II restorations, which typically experience considerable occlusal forces from mastication, use of conventional inflexible, highly filled and hard composites has often led to problems such as creation of marginal gaps. Use of the compositions according to the present invention as liners under such conventional compositions permits their use and avoids such gaps.

Other areas of use of the present inventions which will occur to those of skill in the art include without limitation: use of the compositions under temporary crowns, so-called Class III type restorations, small non-stress Class IV repairs, porcelain veneer bonding, tunnel preparation, splinting, marginal defect repair, deciduous class I or II repair, impart seals, buccal pit restorations, porcelain repair, pit and fissure sealant, adult preventative resin, small core buildup applications, and where maximum strength and polishability is desired.

EXAMPLES

The following examples are given by way of illustration but without limitation. In the following examples, all parts and percentages are by weight unless otherwise noted. Compounds identified herein are compounds purchased from the manufactures indicated in the following list, which list also includes the abbreviations used herein to identify those compounds.

| | |
|---|---|
| Acetone | (Ashland Chemical Inc.). |
| Bis "A" Dima | Bisphenol A dimethacrylate (Esschem Co., Essington, PA) |
| Bis-GMA | Bisphenol A glycidyl methacrylate (Essehem Co., Essington, PA) |
| CQ | Camphorquinone (Hampford Research, Inc., Stratford, Connecticut). |
| Darocur | Darocur 4265 (Ciba-Geigy Corp.Hawthorne, New York) |
| Dima | Ethoxylated Bisphenol A Dimethacrylate (Sartomer Co., Exton, PA)(6mole and 10 mole) |
| EDMAB | 2-Ethyl-4-dimethylaminobenzoate (Aldrich Chemical Company, Milwaukee, Wisconsin). |
| EtOH | Ethanol (AAPER Alcohol & Chemical Co.). |
| 2-HEMA | 2-Hydroxyethyl methacrylate (Rohm & Haas Co.). |
| HPMA | Hydroxypropyl methacrylate (Rohm & Haas Co.). |
| MEHQ | 4-Methoxyphenol (Aldrich Chemical Company, Milwaukee, Wisconsin) |
| Lucrin TPO | (BASF, Charlotte NC) |
| PUDMA | Polyurethane dimethacrylate ester (IRR456), (UCB Chemicals Co., Drogenbos, Belgium). |
| Uvinul 3000 | BASF Corporation, Mount Olive, New Jersey |
| HME | Hexa-function methacrylate ester (Bisco, Inc. Schaumburg, IL) |
| THFMA | Tetrahydrofurfuryl methacrylate (Essehem Co., Essington, PA) |
| t-BPB | tert-butylperoxybenzoate (Elf Atochem North America, Inc., Philadelphia, PA) |
| TEGDMA | Triethyleneglycol dimethacrylate (Esschem Co., Essington, PA) |
| TMPTMA | Trimethylol propane trimethacrylate (Esschem. Co., Essington, PA) |
| UDMA | Urethane dimethacrylate (Esschem Co., Essington, PA) |

The molecular weight (number average) of the some monomer used in the present invention are set out below Molecular Weight of monomers used in low shrink composites.

| | PUDMA | 10 mole Dima | 6 mole Dima | HME ester | Bis-GMA | TEG DMA | THFMA |
|---|---|---|---|---|---|---|---|
| MW | 1500 | 804 | 628 | 977 | 512 | 286 | 170 |
| No. of Functional groups | 2 | 2 | 2 | 6 | 2 | 2 | 1 |

The compositions in the following Examples were tested for their tensile strength (DTS), compressive strength (CS), flexural strength (FS), flexural modulus (FM), wear and water sorption according to the following methods.

1A. Sample Preparation

A diametral tensile strength (DTS) test specimen of the above-identified composition was prepared by filling a 6 mm diameter and 3 mm deep stainless steel cavity mold. The composition was light-cured for 40 seconds on each side (2×40 sec.) using a 500 milliwatt light source such as an Optilux 400, Demetron Research Corp., Dansbury, Conn.) light source.

Compressive Strength (CS) specimen of the same composition was prepared in a similar manner by filling a 4 mm diameter by 6 mm deep two-piece stainless steel mold followed by light curing on each side for 60 seconds (2×60 sec.) using the light powered source and intensity indicated for the DTS specimen.

Flexure strength and flexure modulus of the composition were determined by creating a bar-shaped specimen (25 min×2 mm×2 min) from a two-piece stainless steel mold. Curing was effected using the same light source and intensity indicated above but applied for 2×40 sec. on one side of the mold.

B. Strength and Flexibility Testing

Diametral, tensile strength, compressive strength, flexure strength and flexure modulus were measured by loading each specimen to failure on a Model 4466, Instron Corp., Canton, Mass. for DTS and CS tests and on a QTest 4, NITS Systems, Cary, N.C. for the FS and FM tests. 8 specimens were broken for diametral tensile strength and compressive strength, 5 specimens were broken for flexure strength, and the results averaged. A cross-head speed of 10 mm/min. was used for compression strength and diametral, tensile strength testing, while a cross-head speed of 0.75 mm/min. was used for flexure testing.

Flexure strength measurements are useful in evaluating a material because they involve both tensile and compressive stresses under loading. As the load is applied along the length of the bar-shaped specimen, the side in direct contact with the applied load is subjected to compression, while the opposite parallel side is subjected to tensile forces. Since tooth restorations in the mouth undergo complex stresses, it is of interest to consider tests, which are similar to what occurs naturally. The flexure strength values indicate that the composite becomes more flexible (elastic) as more monomer is added to the resin, although the flexure strength decreases. This increase in elasticity may adversely affect the flexure modulus of a material. Since an increase in elasticity may increase the deflection under a given load, the flexure modulus decreases as the monomer content is added. Flexure modulus values were measured immediately after curing on one set of samples, and after curing and subsequent immersion in water at 37 degrees Centigrade for 24 hours.

Water sorption of the composition was also determined according to ANSI/ADA Specification No. 27 (1993) for resin based filler C. Shrinkage Testing The amount by which the composite shrunk after polymerization (polymerization shrinkage) was measured by using a video-imaging device (AcuVol™; Bisco, Inc.). In using the AcuVol video-imaging device, a composite sample was shaped into a semi-sphere sphere (with volume averaging 12 mm) and placed on the Teflon pedestal in the light path. The sample was allowed to rest for 3 minutes before being light cured for 40 seconds using a light gun (VIP™; Bisco, Inc.). The gun tip was positioned about 1 mm above the top of the sample. The light intensity was set at 500 mW/cm$^2$. The total energy used for polymerization was about 2 J/cm$^2$. Volumetric shrinkage was recorded for ten minutes after the cure. During the measurement, the volume and shrinkage profiles were continuously monitored. Each composite was measured seven times with the average and standard deviation reported. The single-view volumetric reconstruction mode with one angle picture was used for each measurement. The brightness was set at a value of 1 and, 'Find Boundary Mode' was employed as the boundary scheme in the measurement.

D. Wear Testing

Wear resistance was determined by Oral Wear Simulator 2000 (Proto-tech) and analyzed by Surfanalyzer (Sahr Federal Inc.). The composite was cured in a Teflon Mold (~15 mm diameter×3 mm thick) following by polishing with 1500 grit abrasive paper. The stylus was prepared by mounting a ceramic ball on the screw denture based acrylic resin. Using impression material, draw a bead around the top perimeter of the acrylic tube in which the specimen is mounted. The stylus travel distance was about 1 mm. The wear test was set as following conditions

| Settings on Wear Tester | |
| --- | --- |
| Abrasion Force (lower right knob) | 50 (6 lbs.) |
| Attrition Force (lower left knob) | 80 (20 lbs) |
| Abrasion Duration (right middle knob) | 300 |
| Attrition Duration (left middle knob) | 150 |
| Speed Control (on back) | 76 (100 min$^{-1}$) |

After wear test, sample was examined by the Surfanalyzer to determine how deep the composite was worn.

Example 1

A. Diluent Monomer/Photoinitiator

A diluent monomer solution containing a polymerization initiator system and other compounds was formulated by admixing 45.10% 10 mole Dima, 37.73% Hexafunctional Methacrylate, 0.130% MEMHQ, 7.750% EDMAB, 1.890% CQ, and 7.400% Uvinul-3000.

B. Resin Solution

The aforementioned diluent monomer solution and photoinitiator system was combined with PUDMA in the following amounts: 25.6% diluent monomer/photoinitiator system, and 74.4% PUDMA. The mixture was also protected is from light during admixture and was placed in separate, light-opaque syringes immediately after mixture.

C. Composite

In term of total weight of composition, the compositions included total weight percentage of about 11.55 wt % PUDMA, 46.7 wt % of Sr glass, 25.3 wt % of TC3 and 12.7 wt % OX-5O. The filler loading is 84.7 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
| --- | --- | --- | --- | --- | --- | --- |
| Results | 0.86 ± 0.31 | 41.3 ± 3.4 | 58.8 ± 13.5 | 2.1 ± 0.1 | — | — |

Example 2

Dental compositions were formulated according to the following amounts and procedures.

A. Diluent Monomer/Photoinitiator. A diluent monomer solution containing a polymerization initiator system and other compounds was formulated by admixing 30.0% THFMA with 0.149% MEHQ, 51.232% 10 mole Dima, 8.339% EDMAB, 2.084% CQ, and 8.1885% Uvinul-3000. The mixture was protected from light during and after such mixing.

B. Resin Solution. The aforementioned diluent monomer solution and photoinitiator system was combined with PUDMA in the following amounts: 23.2% diluent monomer/photoinitiator system and 76.7% PUDMA The mixture was also protected from light during and after this formulation step. Each admixture was protected from light during admixture and was placed in separate, light-opaque syringes immediately after mixture.

The resultant resin compositions exhibited good viscosity and flowablity, and were easily dispensable from their syringes.

C. Composite

In term of total weight of composition, the compositions included total weight percentage of about 11.55 wt % PUDMA, 46.7 wt % of Sr glass, 25.3 wt % of TC3 and 12.7 wt % OX-5O. The filler loading is 84.7 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
|---|---|---|---|---|---|---|
| Results | 1.02 ± 0.01 | 43.5 ± 3.0 | 61.4 ± 3.5 | 3.1 ± 0.1 | — | — |

Example 3

A. Diluent Monomer/Photoinitiator

A diluent monomer solution containing a polymerization initiator system and other compounds was formulated by admixing 54.97% 6 mole Dima, 36.69% TEGDMA, 0.0074% MEMHQ, 3.706%. EDMAB, 0.9326% CQ, and 3.6400% Uvinul-3000.

B. Resin Solution

The aforementioned diluent monomer solution and photoinitiator system was combined with PUDMA in the following amounts: 52.2% diluent monomer/photoinitiator system, and 47.8% PUDMA The mixture was also protected from light during admixture and was placed in separate, light-opaque syringes immediately after mixture.

C. Composite

In term of total weight of composition, the compositions included total weight percentage of about 7.43 wt % PUDMA, 46.7 wt % of Sr glass, 25.3 wt % of TC3 and 12.7 wt % OX-5O. The filler loading is 84.7 wt %

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
|---|---|---|---|---|---|---|
| Results | 1.64 ± 0.05 | 45.0 ± 3.4 | 119.2 ± 13.9 | 9.7 ± 0.1 | — | About 100 |

Example 4

A. Diluent Monomer/Photoinitiator

A diluent monomer solution containing a polymerization initiator system and other compounds was formulated by admixing 81.481% TEGDMA, 0.148% MEHQ, 8.231% EDMAB, 2.058% CQ, and 8.082% Uvinul-3000.

B. Resin Solution

The aforementioned diluent monomer solution and photoinitiator system was combined with PUDMA and Bis-GMA in the following amounts: 23.5% diluent monomer/photoinitiator system, and 47.8% PUDMA. and 28.7% Bis-GMA. The mixture was also protected from light during admixture and was placed in separate, light-opaque syringes immediately after mixture.

C. Composite

In term of total weight of composition, the compositions included total weight percentage of about 7.43 wt % PUDMA, 46.7 wt % of Sr glass, 25.3 wt % of TC3 and 12.7% OX-5O. The filler loading is 84.7 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
|---|---|---|---|---|---|---|
| Results | 1.45 ± 0.09 | 46.0 ± 4.4 | 111.5 ± 7.8 | 9.7 ± 0.1 | — | >100 |

Example 5

A. Diluent Monomer/Photoinitiator

A diluent monomer solution containing a polymerization initiator system and other compounds was formulated by admixing 36.77% TEGDMA, 15.00% THFMA, 7.20% Bis "A" Dima, 0.031% MEMHQ, 3.00% EDMAB, 0.60% CQ, and 2.4% Uvinul-3000.

B. Resin Solution

The aforementioned diluent monomer solution and photoinitiator system was combined with BisGMA and 6 mole Dima in the following amounts: 25.0% 6 mole Dima and 25.0% Bis-GMA The mixture was also protected from light during admixture and was placed in separate, light-opaque syringes immediately after mixture.

C. Composite

In term of total weight of composition, the compositions included total weight percentage of about 7.65 wt % Bis-GMA and 6 mole Dina., 47.8 wt % of Sr glass, 21.8 wt % of TC3 and 17.4 wt % OX-5O. The filler loading is 87 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
|---|---|---|---|---|---|---|
| Results | 1.51 ± 0.04 | 50.3 ± 2.7 | 134.8 ± 25.8 | 12.9 ± 0.2 | 295.7 ± 17.5 | 58 ± 8 |

Example 6

A. Diluent Monomer/Photoinitiator

A diluent monomer solution containing a polymerization initiator system and other compounds was formulated by admixing 82.96% TEGDMA, 8.00% Bis "A" Dima, 0.040% MEMHQ 3.00% EDMAB, 1.00% CQ, and 5.00% Uvinul-3000.

B. Resin Solution

The aforementioned diluent monomer solution and photoinitiator system was combined with Bis-GMA and 6 mole Dima in the following amounts: 25.0% diluent monomer/photoinitiator system, 70.0% of 6 mole Dima and 5.0% Bis-GMA. The mixture was also protected from light during admixture and was placed in separate, light-opaque syringes immediately after mixture.

C. Composite

In term of total weight of composition, the compositions included total weight percentage of about 11.27 wt % Bis-GMA and 6 mole Dima., 46.7 wt % of Sr glass, 25.3 wt % of TC3 and 32.7% OX-5O. The filler loading is 84.7 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
|---|---|---|---|---|---|---|
| Results | 1.42 ± 0.04 | 51.3 ± 3.5 | 111.7 ± 13.7 | 13.9 ± 0.3 | — | 41 ± 12 |

Example 7

A. Diluent Monomer/Photoinitiator

A diluent monomer solution containing a polymerization initiator system and other compounds was formulated by admixing 55.28% 10 mole Dima, 27.54% THFMA, 0.09% MEHQ, 7.76% EDMAB, 2.57% CQ, and 5.62% Uvinul-3000, and 1.14% t-BPB.

B. Resin Solution

The aforementioned diluent monomer solution and photoinitiator system was combined with PUDMA in the following amounts: 21.8% diluent monomer/photoinitiator system, and 78.2% PUDMA. The mixture was also protected from light during admixture and was placed in separate, light-opaque syringes immediately after mixture.

C. Composite

In terms of total weight of the composition, the compositions included total weight percentage of about 11.73% PUDMA, 46.7 wt % of Sr glass, 25.3 wt % of TC3 and 12.7 wt % OX-5O. The filler loading is 84.7 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
|---|---|---|---|---|---|---|
| Results | 1.03 ± 0.01 | 40.3 ± 3.5 | 77.0 ± 7.3 | 3.4 ± 0.2 | — | — |

Example 8

A. Diluent Monomer/Photoinitiator.

A diluent monomer solution containing a polymerization initiator system and other compounds was formulated by admixing 55.28% 10 mole Dima, 27.54% THFMA, 0.09% MEHQ, 6.98% EDMAB, 1.74% CQ, and 5.62% Uvinul-3000, and 2.75% TPO.

B. Resin Solution

The aforementioned diluent monomer solution and photoinitiator system was combined with PUDMA in the following amounts: 21.8% diluent monomer/photoinitiator system, and 78.2% PUDMA. The mixture was also protected from light during admixture and was placed in separate, light-opaque syringes immediately after mixture.

C. Composite

In terms of toal weight of the composition, the compositions included total weight percentage of about 11.73% PUDMA, 46.7 wt % of Sr glass, 25.3 wt % of TC3 and 12.7 wt % OX-5O. The filler loading is 84.7 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
|---|---|---|---|---|---|---|
| Results | 1.06 ± 0.03 | 42.1 ± 3.0 | 76.7 ± 3.7 | 3.2 ± 0.2 | — | — |

Example 9

A. Diluent Monomer/Photoinitiator

A diluent monomer solution containing a polymerization initiator system and other compounds was formulated by admixing 55.28% 10 mole Dima, 27.54% THFMA, 0.09% MEHQ, 7.16%, EDMAB, 1.79% CQ, and 5.62% Uvinul-3000, 1.14% t-BPB, and 1.38% TPO.

B. Resin Solution

The aforementioned diluent monomer solution and photoinitiator system was combined with PUDMA in the following amounts: 21.8% diluent monomer/photoinitiator system, and 78.2% PUDMA. The mixture was also protected from light during admixture and was placed in separate, light-opaque syringes immediately after mixture.

C. Composite

In terms of total weight of the composition, the compositions included total weight percentage of about 11.73 wt % PUDMA, 46.7 wt % Sr glass, 25.3 wt % of TC3 and 12.7 wt % OX-5O. The filler loading is 84.7 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm |
|---|---|---|---|---|---|---|
| Results | 1.03 ± 0.02 | 39.5 ± 2.5 | 73.0 ± 1.6 | 3.6 ± 0.3 | — | — |

Example 10

A. Diluent Monomer/Photoinitiator.

A diluent monomer solution containing a polymerization initiator system and other compounds was formulated by admixing 81.66% TEGDMA, 8.00% Bis"A"Dima, 0.040% MEHQ, 3.00% EDMAB, 0.30% CQ, 2.00% TPO and 5.00% Uvinul-3000.

B. Resin Solution

The aforementioned diluent monomer solution and photoinitiator system was combined with Bis-GMA and 6 mole Dima in the following amounts: 25.0% diluent monomer/photoinitiator system, 70.0% 6 mole Dima, and 5.0% Bis-GMA. The mixture was also protected from light during admixture and was placed in separate, light-opaque syringes immediately after mixture.

C. Composite

In terms of total weight of the composition, the compositions included 13.5% of the above resin, 46.909 wt % of Sr glass, 21.625 wt % of TC3, 15.570 wt % OX-5O, 0.277 wt % yellow tint, 0.173 wt % red tint and 0.216 black tint dyes. The filler loading is 86.5 wt %.

D. Composite Properties

| Properties | Shrinkage n = 3 (Vol %) | DTS n = 8 MPa | Flexural Strength N = 5 MPa | Flexural Modulus n = 5 GPa | Compressive Strength n = 5 MPa | Wear n = 6 Attrition μm | Water Sorption n = 5 μg/mm³ |
|---|---|---|---|---|---|---|---|
| Results | 1.5 ± 0.02 | 50.0 ± 7.0 | 140.0 ± 21.3 | 14.6 ± 0.3 | 276.5 ± 36.6 | 38 ± 8 | 6 |

Example 11

As an example of a composite including a glass fiber component according to the preceding Example, the following composite was prepared.

A. Diluent Monomer/Photoinitiator

A diluent monomer solution containing a polymerization initiator system and other compounds was formulated by admixing 82.96% TEGDMA, 8.00% Bis "A" Dima, 0.040% MEHQ, 3.00% EDMAB, 1.00% CQ and 5.00.% Uvinul-3000.

B. Resin Solution

The aforementioned dilnent monomer solution and photoinitator system was combined with Bis-GMA and 6 mole Dima in the following amounts: 25.0% diluent monomer/photoinitiator system, 70.0% 6 mole Dima and 5.0% Bis GMA. The mixture was also protected from light during admixture and was placed in separate, light-opaque syringes immediately after mixture.

C. Composite

In terms of total weight of the composition, the compositions included 8.00% above resin, 46.03 wt % of Fiberfrax, 29.24 wt % of TC3 and 16.73% OX-50. The filler loading is 92.00 wt %.

D. Composite Properties

| Properties | Shrinkage n = 3 (Vol %) | DTS n = 8 MPa | Flexural Strength n = 5 MPa | Flexural Modulus n = 5 GPa | Compressive Strength n = 5 MPa | Wear n = 6 Attrition μm |
|---|---|---|---|---|---|---|
| Results | 1.05 ± 0.02 | 42.2 ± 4.0 | 97.2 ± 8.3 | 19.2 ± 0.8 | 285.3 ± 12.7 | — |

Example 12

A composite according to Example 10 was compared with various commercial composite products in terms of polymerization shrinkage. The following results were observed:

TABLE 1

The shrinkages (% Volume) of Commercial Composites and Example 10 Composite

| Kerr .4 | 3 M Filtek P-60 | Kerr Herculite XRV | Dentsply Esthetx | 3 M Z100 | Discus Dental Matrix | 3 m Filtek Z-250 | Vivadent Heliomolar | Example 10 Composite |
|---|---|---|---|---|---|---|---|---|
| 3.4 | 2.9 | 2.9 | 2.8 | 2.7 | 2.3 | 2.2 | 2.2 | 1.5 |

A composite according to Example 10 was compared with a commercial composite reportedly utilizing a spherical filler component. The following results were observed:

TABLE 2

Comparison of Example 10 Composite and Commercial Spherical Composite

| | Composite of Example 10 | Palfique Estelite |
|---|---|---|
| Filler Load (% by volume) | 74 | NA |
| Filler Load (% by weight) | 86.5 | 82 |
| Filler Type | Sr Glass, Spherical Filler | Spherical Silica-Zirconia |
| Volumetric Shrinkage % | 1.5 | 2.0 |
| Microstrain (μm/m) | 1118 ± 50 | — |
| DTS (Mpa) | 50 ± 7.0 | 36.5 ± 9.5 |
| Flexural Strength (Mpa) | 140 ± 21.3 | 61.5 ± 16.5 |
| Flexural Modulus (GPa) | 14.6 ± 0.3 | 6.5 ± 0.5 |
| Compressive Strength (MPa) | 276.5 ± 36.6 | 305.1 ± 44.1 |

As indicated above and in the below Table 3, composite of the present invention exhibits lower shrinkage with better flexibility and other properties than current commercial composites. By using the formulation of the present invention, a much lower (about 1.8% or less by volume fraction) shrinkage is obtained in the resulting composite as compared with commercial universal hybrid composites, which shrink from 2.0 to 3.5% by volume fraction (see Tables 1–3). The above test values also demonstrate that the compositions according to the present invention exhibited good flexibility and tensile strengths.

As can also be seen below in Table 3, the present invention's shrinkage values are well below those for conventional filled composites. The observed low modulus values for the compositions of the present invention, considered along with its good flexibility and tensile strength and compression strength, indicate that these compositions are well suited as a restorative material in Class I, II, IV, V restorations and core build-ups and other applications involving shear and tensile stresses.

The ability of composites according to the present invention to dissipate internal skrinkage-induced stresses was also evaluated along with that of certain commercial composites according to the following test protocol.

An indirect technique to measure contraction stress built up in dental composite was constructed. A microstrain gauge was applied onto an acrylic ring to obtain the strain data as a representation of the contraction stress caused by the composite shrinkage as follows. A 3800 Strain Indicator with Model 2000 A/D Converter (Measurements Group, Raleigh, N.C.), and a strain gages (EA-13-062AP-120 or EA-06-062AP-120) were employed. The acrylic ring (9.6 mm OD and 6.3 mm ID) is cut into a 2.0 mm thick ring using the Isomet diamond saw. After briefly roughening the inner wall with 300 grit sand paper, Bisco One-Step adhesive is applied on to it twice following by 10 s light cure at 500 mW/cm². The strain gage is attached to outside wall of acrylic ring using adhesive. A small amount (less than ½) of composite is added into the ring to fill the bottom, and the composite is cured for 40 s at 500 mW/cm². After 20 min, the microstrain data is read from the Strain Indicator. The following results were observed.

TABLE 3

A Comparison for Volumetric Shrinkage and Microstrain of Low Shrinkage Composite and Commercial Composites]

| Composites | Example 1–11 Composites | Z100 | Herculite XRV | Helio-molar | TPH Spectrum |
|---|---|---|---|---|---|
| Shrinkage Vol % | 0.9–1.5 ± 0.02 | 2.7 ± −0.1 | 2.9 ± 0.1 | 2.2 ± 0.1 | 3.6 ± .1 |
| Microstrain μm/m | 470–950 | 1730 ± 30 | 1400 ± 90 | 730 ± 50 | 1420 ± 60 |

To those skilled in the art to which this invention relates, other changes in construction and different embodiments and applications of the invention will suggest themselves without departing from the spirit and scope of the invention. The foregoing disclosures and the descriptions herein are illustrative and are not intended to be in any sense limiting.

What is claimed is:

1. A dental composite composition comprising:
   (a) from about 1 to about 35 weight percent of a monomer portion comprising at least one monomer having a functional group capable of undergoing polymerization;
   (b) from about 75 to about 95 weight percent of a filler portion, said filler portion comprising
      a spherical filler portion at a concentration of about 5 weight percent to about 75 weight percent of the composition, having an average size of about 0.2 microns to about 1.5 microns;
      a submicron filler portion at a concentration of about 5 weight percent to about 50 weight percent of the composition, having an average size of about 0.020 microns to about 0.080 microns; and
      a conventional filler portion at a concentration of about 5 weight percent to about 75 weight percent of the composition; and
   (c) from about 0.01 to about 10 weight percent of a polymerization catalyst portion comprising at least one catalyst capable of assisting in the polymerization of said functional group of said monomer portion and hardening of the composition after application of the composition to a tooth surface or other dental surface;
      wherein said spherical filler portion is present in an amount sufficient to reduce shrinkage of the composition after polymerization to about 1.8 percent or less.

2. The composition of claim 1, wherein said spherical filler portion comprises from about 20 to about 40 weight percent of the composition.

3. The composition of claim 2, wherein said filler portion comprises from about 80 to about 92 weight percent of the composition and the composition exhibits shrinkage after polymerization of about 1.5 percent or less.

4. The composition of claim 3, wherein the at least one monomer having a functional group capable of undergoing polymerization comprises TEGDMA, Bis-GMA, and ethoxylated bisphenol A dimethacrylate.

5. The composition of claim 1, wherein said spherical filler portion comprises from about 20 to about 30 weight percent of the composition.

6. The composition of claim 5, wherein said filler portion comprises from about 84 to about 92 weight percent of the composition and the composition exhibits a shrinkage about 1% or less after polymerization.

7. The composition of claim 1, wherein said spherical filler portion comprises from about 20 to about 25 weight percent of the composition.

8. The composition of claim 7, wherein said filler portion comprises from about 84 to about 92 weight percent of the composition and the composition exhibits a shrinkage of less than 1 percent after polymerization.

9. The composition of claim 1, wherein said spherical filler portion comprises one or more spherical filler particles selected from the group comprising silanated aluminum oxide, zirconium oxide, silicon oxide, barium glass, strontium glass and silicate glasses.

10. The composition of claim 1, wherein said spherical filler portion comprises two or more suitable spherical filler particles having an average particle size of from about 0.2 to 1.5 microns.

11. The composition of claim 1, wherein the filler portion comprises a spherical filler portion comprising from about 20 to about 75 weight percent of the composition and a submicron filler portion that comprises from about 5 to about 50 weight percent of the composition.

12. The composition of claim 1, wherein the filler portion comprises a spherical filler portion comprising from about 25 to about 75 percent of the composition and a submicron filler portion that comprises from about 20 to about 40 weight percent the composition.

13. The composition of claim 1, wherein the filler portion comprises a spherical filler portion comprising from about 60 to about 75 weight percent of the composition and a submicron filler portion that comprises from about 20 to about 40 weight percent the composition.

14. The composition of claim 1, wherein said filler portion comprises from about 10 to about 50 weight percent of a spherical filler portion, from about 5 to about 40 weight percent of a submicron filler portion and from about 40 to about 85 weight percent of a conventional filler portion.

15. The composition of claim 1, wherein said filler portion comprises from about 20 to about 40 weight percent of a spherical filler portion, from about 10 to about 30 weight percent of a submicron filler portion and from about 45 to about 60 weight percent of a conventional filler portion.

16. The composition of claim 1, wherein said filler portion comprises from about 20 to about 30 weight percent of a spherical filler portion, from about 15 to about 25 weight percent of a submicron filler portion and from about 45 to about 55 weight percent of a conventional filler portion.

17. The composition of claim 1, wherein said monomer portion comprises at least one multifunctional comonomer portion.

18. The composition of claim 17, wherein said multifunctional comonomer portion comprises a polyurethane methacrylate oligomer portion.

19. The composition of claim 18, wherein said polyurethane methacrylate oligomer portion is a polyurethane dimethacrylate oligomer.

20. The composition of claim 19, wherein said polyurethane dimethacrylate oligomer comprises from about 1 to about 14 weight percent of the composition.

21. The composition of claim 17, wherein said multifunctional comonomer portion is PUDMA.

22. The composition of claim 1, wherein the at least one monomer having a functional group capable of undergoing polymerization comprises at least one multifunctional comonomer portion and at least one monofunctional monomer portion.

23. The composition of claim 22, wherein said multifunctional comonomer portion is PUDMA.

24. The composition of claim 1, wherein the at least one monomer having a functional group capable of undergoing polymerization comprises at least two multifunctional comonomers.

25. The composition of claim 24, wherein one of said multifunctional comonomers is a polyurethane methacrylate oligomer.

26. The composition of claim 25, wherein said polyurethane methacrylate oligomer is a polyurethane dimethacrylate oligomer.

27. The composition of claim 26, wherein said polyurethane dimethacrylate oligomer comprises from about 1 to about 14 weight percent of the composition.

28. The composition of claim 24, wherein the at least two multifunctional comonomers comprise TEGDMA, Bis-GMA, and ethoxylated bisphenol A dimethacrylate.

29. The composition of claim 1, wherein said monomer portion comprises THFMA.

30. The composition of claim 1, wherein the filler portion further comprises a glass fiber portion.

31. The composition of claim 30, wherein the glass fiber portion is present at a concentration of about 20 weight percent to about 80 weight percent of the composition.

32. A method of restoring a tooth, the method comprising:
  (a) cleaning and preparing the surface of the tooth to be restored;
  (b) applying to the prepared tooth surface a dental composite composition comprising;
    (1) from about 1 to about 35 weight percent of a monomer portion comprising at least one monomer having a functional group capable of undergoing polymerization;
    (2) from about 75 to about 95 weight percent of a filler portion, said filler portion comprising
      a spherical filler portion at a concentration of about 5 weight percent to about 75 weight percent of the composition, having an average size of about 0.2 microns to about 1.5 microns;
      a submicron filler portion at a concentration of about 5 weight percent to about 50 weight percent of the composition, having an average size of about 0.020 microns to about 0.080 microns; and
      a conventional filler portion at a concentration of about 5 weight percent to about 75 weight percent of the composition; and
    (3) from about 0.01 to about 10 weight percent of a polymerization catalyst portion comprising at least one catalyst capable of assisting in the polymerization of said functional group of said monomer portion and hardening of the composition after application of the composition to a tooth surface or other dental surface;
      wherein said spherical filler portion is present in an amount sufficient to reduce shrinkage of the composition after polymerization to about 1.8 percent or less; and
  (c) causing the composition to polymerize and harden on the prepared tooth surface.

33. The method of claim 32, wherein said polymerization is initiated by directing a suitable light source to the applied composite composition.

34. A method of restoring a tooth, the method comprising:
  (a) cleaning and preparing the tooth surface,
  (b) applying to the prepared surface a layer of a composite composition comprising,
    (1) from about 1 to about 35 weight percent of a monomer portion comprising at least one monomer having a functional group capable of undergoing polymerization;
    (2) from about 75 to about 95 weight percent of a filler portion, said filler portion comprising
      a spherical filler portion at a concentration of about 5 weight percent to about 75 weight percent of the composition, having an average size of about 0.2 microns to about 1.5 microns;
      a submicron filler portion at a concentration of about 5 weight percent to about 50 weight percent of the composition, having an average size of about 0.020 microns to about 0.080 microns; and
      a conventional filler portion at a concentration of about 5 weight percent to about 75 weight percent of the composition; and
    (3) from about 0.01 to about 10 weight percent of a polymerization catalyst portion comprising at least one catalyst capable of assisting in the polymerization of said functional group of said monomer portion and hardening of the composition after application of the composition to a tooth surface or other dental surface;
      wherein said spherical filler portion is present in an amount sufficient to reduce shrinkage of the composition after polymerization to about 1.8 percent or less;

(c) causing the composition to at least partially polymerize, and (d) applying a filled restorative material to said at least partially polymerized composition layer and causing the restorative material to polymerize and harden.

35. A method of restoring a tooth comprising by applying a dental appliance thereto, the method comprising:

(a) cleaning and preparing the tooth surface, (b) applying to the dental appliance and/or to the prepared surface a dental composite composition comprising (1) from about 1 to about 35 weight percent of a monomer portion comprising at least one monomer having a functional group capable of undergoing polymerization;

(2) from about 75 to about 95 weight percent of a filler portion, said filler portion comprising a spherical filler portion at a concentration of about 5 weight percent to about 75 weight percent of the composition, having an average size of about 0.2 microns to about 1.5 microns;

a submicron filler portion at a concentration of about 5 weight percent to about 50 weight percent of the composition, having an average size of about 0.020 microns to about 0.080 microns; and a conventional filler portion at a concentration of about 5 weight percent to about 75 weight percent of the composition; and (3) from about 0.01 to about 10 weight percent of a polymerization catalyst portion comprising at least one catalyst capable of assisting in the polymerization of said functional group of said monomer portion and hardening of the composition after application of the composition to a tooth surface or other dental surface;

wherein said spherical filler portion is present in an amount sufficient to reduce shrinkage of the composition after polymerization to about 1.8 percent or less; and, (c) applying the appliance to the prepared surface of the tooth, and (d) causing the composition to polymerize and harden and to affix the appliance to the tooth.

\* \* \* \* \*